(12) United States Patent
Yonaha et al.

(10) Patent No.: US 10,896,764 B2
(45) Date of Patent: Jan. 19, 2021

(54) DRUG INSPECTION APPARATUS AND METHOD

(71) Applicant: FUJIFILM TOYAMA CHEMICAL CO., LTD., Tokyo (JP)

(72) Inventors: Makoto Yonaha, Ashigarakami-gun (JP); Tetsuya Takamori, Ashigarakami-gun (JP); Ippei Takahashi, Ashigarakami-gun (JP); Seigo Sugimoto, Ashigarakami-gun (JP)

(73) Assignee: FUJIFILM TOYAMA CHEMICAL CO., LTD., Tokyo (JP)

( * ) Notice: Subject to any disclaimer, the term of this patent is extended or adjusted under 35 U.S.C. 154(b) by 88 days.

(21) Appl. No.: 14/633,499

(22) Filed: Feb. 27, 2015

(65) Prior Publication Data

US 2015/0170373 A1 Jun. 18, 2015

Related U.S. Application Data

(63) Continuation of application No. PCT/JP2013/073959, filed on Sep. 5, 2013.

(30) Foreign Application Priority Data

Sep. 27, 2012 (JP) ................. 2012-213633

(51) Int. Cl.
*G06K 9/00* (2006.01)
*G06T 7/00* (2017.01)
(Continued)

(52) U.S. Cl.
CPC ............. *G16H 70/40* (2018.01); *G06K 9/00* (2013.01); *G06T 7/001* (2013.01); *G06T 7/20* (2013.01);
(Continued)

(58) Field of Classification Search
CPC . G06F 19/3456; G06F 19/3462; G16H 20/10; G06K 9/00; G06K 2209/19; G06T 7/001; G06T 2207/30242
See application file for complete search history.

(56) References Cited

U.S. PATENT DOCUMENTS 6,529,892 B1 * 3/2003 Lambert ............... G16H 20/10
706/55
2009/0178857 A1 7/2009 Yuyama et al.
(Continued)

FOREIGN PATENT DOCUMENTS

JP 9-299448 A 11/1997
JP 10-162116 A 6/1998
(Continued)

OTHER PUBLICATIONS

International Search Report, issued in PCT/JP2013/073959, dated Oct. 8, 2013.
(Continued)

*Primary Examiner* — Kenny A Cese
(74) *Attorney, Agent, or Firm* — Birch, Stewart, Kolasch & Birch, LLP

(57) ABSTRACT

A drug inspection apparatus inspects drugs that are prepared based on prescription information and are packaged in a prescription bag. A drug database includes drug images of drugs that can be prepared. A comparison target selection section acquires drug images of drugs, which are prepared according to the prescription, and drugs similar thereto from the drug database. A first drug determination section compares captured images of prepared drugs with the drug images acquired from the drug database, and determines drugs present in the captured images and the number thereof. An inspection result determination section determines whether or not the prepared drugs and the number thereof
(Continued)

match the prescription information based on the prescription information.

20 Claims, 9 Drawing Sheets

(51) Int. Cl.
*G16H 70/40* (2018.01)
*G16H 10/60* (2018.01)
*G16H 20/13* (2018.01)
*G06T 7/20* (2017.01)

(52) U.S. Cl.
CPC ............ *G16H 10/60* (2018.01); *G16H 20/13* (2018.01); *G06K 2209/19* (2013.01); *G06T 2207/30242* (2013.01)

(56) References Cited

U.S. PATENT DOCUMENTS

| | | | | |
|---|---|---|---|---|
| 2012/0200596 | A1* | 8/2012 | Gotou | B07C 5/38 345/625 |
| 2013/0342676 | A1* | 12/2013 | Amano | B65B 57/10 348/86 |
| 2017/0264867 | A1* | 9/2017 | Amano | G01N 21/9508 |

FOREIGN PATENT DOCUMENTS

| | | | | |
|---|---|---|---|---|
| JP | 11-206855 | A | | 8/1999 |
| JP | 2002-279068 | A | | 9/2002 |
| JP | 2004-167158 | A | | 6/2004 |
| JP | 2005-195496 | A | | 7/2005 |
| JP | 3771652 | B2 | * | 4/2006 |
| JP | 2006-142666 | A | | 7/2009 |
| JP | 2014126029 | A | * | 7/2014 |
| WO | WO 2011/112606 | A1 | | 9/2011 |
| WO | WO 2011112606 | A1 | * | 9/2011 ................. A61J 7/04 |
| WO | WO 2012/056317 | A2 | | 5/2012 |
| WO | WO 2012056317 | A2 | * | 5/2012 ............ A61J 7/0084 |
| WO | WO-2012056317 | A2 | * | 5/2012 ............ G06K 9/2036 |

OTHER PUBLICATIONS

Written Opinion of the International Searching Authority, issued in PCT/JP2013/073959, dated Oct. 8, 2013.
Japanese Office Action for Japanese Application No. 2012-213633, dated Mar. 8, 2016, with an English translation.
Extended European Search Report, dated Apr. 15, 2016, for European Application No. 13841952.8.
Japanese Notice of Reasons for Rejection and English translation thereof, dated Sep. 1, 2015, for Japanese Application No. 2012-213633.
Chinese Office Action dated Sep. 5, 2017 for Chinese Application No. 201380044629.X with English translation.
European Office Action for corresponding European Application No. 13841952.8, dated Jun. 19, 2018.
Chinese Office Action for Chinese Application No. 201380044629. X, dated Feb. 25, 2019, with English translation.
European Patent Office Summons to attend oral proceedings pursuant to Rule 115 (1) EPC, dated Apr. 30, 2020, in European Application No. 13841952.8.
Chinese Office Action dated Jul. 3, 2019 in Chinese Patent Application No. 201380044629.X, with English translation.
European Decision to refuse a European Patent application for European Application No. 13841952.8, dated Nov. 11, 2020.

* cited by examiner

FIG. 2

DRUG DB

| ID | DRUG NAME | DRUG IMAGE | SIMILAR DRUG LIST | SIMULTANEOUSLY INDISTINGUISHABLE DRUG LIST |
|---|---|---|---|---|
| 001 | DRUG A | (IMAGE) | DRUGS X, Y | DRUGS D, E |
| 002 | DRUG B | (IMAGE) | DRUGS X, Z | NONE |
| 003 | DRUG C | (IMAGE) | NONE | NONE |
| 004 | ... | | | |

FIG. 3

PRESCRIBED DRUGS    DRUGS TO BE COMPARED
| DRUGS A, B, C |    | DRUGS A, B, C, X, Y, Z |

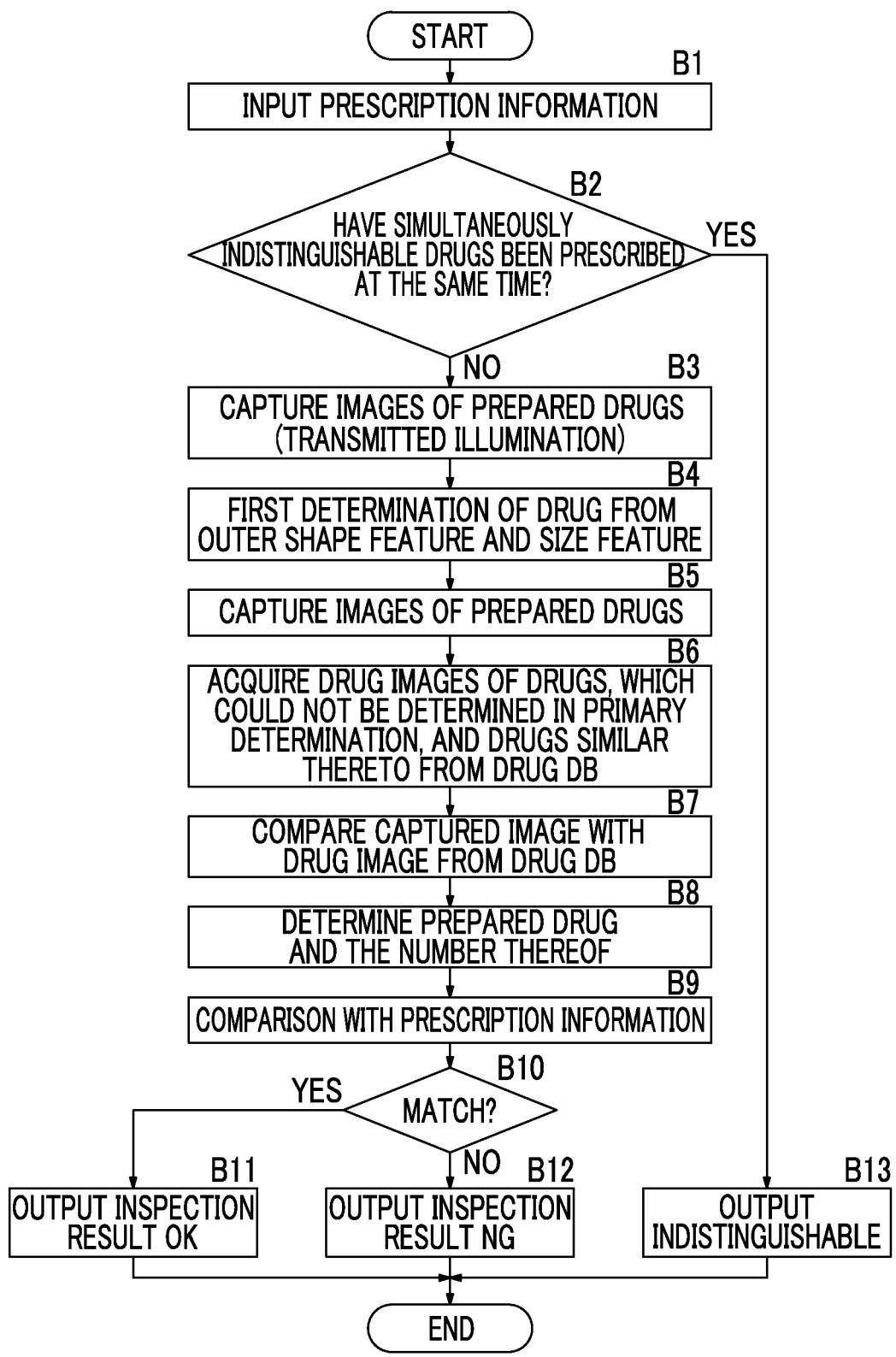

DRUG INSPECTION APPARATUS AND METHOD

CROSS-REFERENCE TO RELATED APPLICATIONS

This application is a Continuation of PCT International Application No. PCT/JP2013/073959 filed on Sep. 5, 2013, which claims priority under 35 U.S.C §119(a) to Japanese Patent Application No. 2012-213633 filed on Sep. 27, 2012. Each of the above applications is hereby expressly incorporated by reference, in its entirety, into the present application.

BACKGROUND OF THE INVENTION

1. Field of the Invention

The present invention relates to a drug inspection apparatus and method, and more particularly, to a drug inspection apparatus and method for inspecting whether or not drugs dispensed according to a prescription are the same as the prescription.

2. Description of the Related Art

In recent years, separation of drug dispensing from the medical practice has been in progress. Accordingly, it is common for a patient to have a checkup in a medical institution and then bring a prescription written by the doctor to a pharmacy so that drugs can be prepared according thereto. In preparation, a plurality of drugs may be packaged in a container (hereinafter, also referred to as a prescription bag), such as a drug bag. During packaging, a plurality of drugs that should be taken at each specified dosage time, for example, at each specified dosage time in the morning, daytime, and evening, are packaged in one prescription bag.

In the packaging of drugs, for patient safety, a pharmacist inspects whether or not packaged drugs have been prepared according to the prescription written by a doctor. As a device for supporting the inspection of the pharmacist, for example, there is a device disclosed in JP1998-162116A (JP-H10-162116A). In JP1998-162116A (JP-H10-162116A), when sequentially transporting drugs packaged in prescription bags according to the prescription, the drugs in the prescription bags being transported are sequentially imaged and the captured images of the drugs in the prescription bags are displayed. In addition, image data of drugs to be prescribed is read from an image database and is displayed. In this case, an image of each drug in the prescription bag being transported and an image read from the database are displayed at the same time for a predetermined time or longer.

A pharmacist inspects whether or not drugs are contained in the prescription bags as prescribed by comparing an image, which is obtained by actually capturing the image of the drug transported on the conveyor belt, with a graphic image (which is displayed simultaneously with the image) of the drug, which is written in a prescription and should be contained in a prescription bag, and visually recognizing the outer shape of each drug and the identification code printed on the outer surface of each drug. JP1998-162116A (JP-H10-162116A) also discloses that whether or not drugs have been correctly packaged according to the prescription, the drugs may be automatically inspected by a computer by causing the computer to perform image processing on an image captured by a camera to compare the image with image data from the image database.

SUMMARY OF THE INVENTION

Here, in JP1998-162116A (JP-H10-162116A), pinpoint comparison between the captured image of the drug in the prescription bag and the image of the drug written in the prescription is performed. In particular, given that image recognition is performed using a computer, there are drugs having very similar appearances (for example, similar shapes, colors, or sizes). In this case, when the wrong drugs that are very similar are prepared by mistake, the possibility that erroneous determination indicating that an inspection result is OK will be made, even though the wrong drugs are packaged, in fact is increased. On the other hand, when determination is made by comparing the images of all drugs, the time required for determination becomes too long since there are many drugs.

In order to solve the aforementioned problem, it is an object of the present invention to provide a drug inspection apparatus and method for realizing efficient inspection while suppressing erroneous determination upon inspection of the drugs.

In order to achieve the aforementioned object, according to an aspect of the present invention, there is provided a drug inspection apparatus for inspecting drugs, which are prepared based on prescription information and are packaged in a prescription bag, including: a comparison target selection section configured to acquire drug images of drugs prepared according to a prescription and drugs similar to the drugs prepared according to the prescription from a drug database that stores drug images of drugs that can be prepared; a first drug determination section configured to perform a comparison of a captured image obtained by capturing an image of prepared drugs with the drug images acquired from the drug database and determining to which drug each drug present in the captured image corresponds and the number of drugs; and an inspection result determination section configured to determine whether or not the prepared drugs and the number of the prepared drugs match the prescription information based on the prescription information.

In the aspect of the present invention, the captured image may be an image obtained by capturing an image of a prescription bag in which the prepared drugs are packaged.

Drugs to be taken at each specified dosage time may be packaged in the prescription bag to be inspected.

The inspection result determination section may determine whether or not the drugs packaged in the prescription bag and the number of drugs match the prescription information for each specified dosage time.

The first drug determination section may extract characters from the captured image, recognize the characters, and determine drugs present in the captured image based on the recognized characters.

When a plurality of drugs which are determined not to be able to be distinguished simultaneously are prescribed at the same time in the prescription, the inspection result determination section may determine that the determination regarding whether or not the prepared drugs and the number thereof match the prescription information is not possible with out the comparison by the first drug determination section.

In addition, the first drug determination section may compare a feature amount difference between the captured image and a drug image which has a feature amount closest to a feature amount extracted from the captured image, with a feature amount difference between the captured image and a drug image having a feature amount second closest to the feature amount extracted from the captured image and determine that drug determination is not possible when both of the differences are approximately the same, and the inspection result determination section may determine that determination regarding whether or not the prepared drugs and the number thereof match the prescription information is possible.

When the inspection result determination section determines that the determination regarding whether or not the prepared drugs and the number thereof match the prescription information is not possible, an indication that that the determination is not possible may be printed on a prescription bag corresponding to a drug determined to be indistinguishable using ink that cannot be visually recognized under visible light.

When the inspection result determination section determines that the determination regarding whether or not the prepared drugs and the number thereof match the prescription information is not possible, the captured image and a drug image from the drug database may be displayed to prompt a user to input a checking result.

The comparison target selection section may acquire images of drugs included in the prescription information and drugs similar to those included in the prescription information from the drug database based on the prescription information.

In addition to those described above, the comparison target selection section may acquire, based on dispensing information for specifying drugs used at the time of at the time of preparation, drug images of drugs included in the dispensing information and drugs similar to the drugs included in the dispensing information from the drug database.

The comparison target selection section may acquire drug images of drugs, which are located at a distance within a predetermined threshold value from a position in a feature space of prepared drugs, as the drug images of the drugs similar to the prepared drugs.

A list of drugs similar to each drug may be stored in the drug database, and the comparison target selection section may acquire the drug images of the drugs similar to the prepared drugs with reference to the list of similar drugs.

The drug inspection apparatus according to the aspect of the present invention may further include a second drug determination section configured to perform primary drug determination by extracting an outer shape feature and a size feature of each drug from the captured images of the prepared drugs and comparing the extracted outer shape feature and the extracted size feature with an outer shape feature and a size feature of each of the drugs to be prepared. In this case, the first drug determination section may compare the captured image with the drug image acquired from the drug database for each drug that cannot be determined by the second drug determination section.

The second drug determination section may extract an outer shape feature and a size feature from a captured image that is captured by emitting illumination light to the prepared drugs from an opposite side to imaging means.

When two or more drugs having similar outer shape features and size features are included in the prescription information, the second drug determination section may determine the two or more similar drugs to be indistinguishable drugs.

When the inspection result determination section determines that the prepared drugs and the number thereof match the prescription information, printing for indicating that an inspection result is OK may be performed on a prescription bag corresponding to the drugs determined to match the prescription information.

When the inspection result determination section determines that the prepared drugs and the number thereof do not match the prescription information, printing for indicating that an inspection result is NG may be performed on a prescription bag corresponding to drugs determined not to match the prescription information using ink that cannot be visually recognized under visible light.

When the inspection result determination section determines that the prepared drugs and the number thereof do not match the prescription information, the captured image and a drug image from the drug database may be displayed to prompt a user to input a checking result.

The drug inspection apparatus according to the aspect of the present invention may further include: a database registration section configured to prompt a user to designate a partial image of each prepared drug included in the captured image and for additionally registering the designated partial image in the drug database when there is no drug image of the prepared drugs in the drug database.

The drug inspection apparatus according to the aspect of the present invention may further include a database registration section configured to acquire drug images of the prepared drugs by accessing a remote master database when there is no image of the prepared drugs in the drug database.

In addition, according to another aspect of the present invention, there is provided a drug inspection method for inspecting drugs, which are prepared based on prescription information and are packaged in a prescription bag, including: acquiring drug images of drugs prepared according to a prescription and drugs similar to the drugs prepared according to the prescription from a drug database, which stores drug images of drugs that can be prepared; comparing a captured image obtained by capturing an image of the prepared drugs with the drug images acquired from the drug database and determining to which drug each drug present in the captured image corresponds and the number of drugs by a drug inspection apparatus; and determining whether or not the prepared drugs and the number of the prepared drugs match the prescription information based on the prescription information by the drug inspection apparatus.

In the drug inspection apparatus and method according to the aspects of the present invention, a captured image obtained by capturing prepared drugs is compared with drug images of drugs prepared according to the prescription and drugs similar thereto, and the drugs and the number thereof are determined. By expanding the image checking target to the range including not only drugs to be prepared according to the prescription but also drugs similar thereto, it is possible to reduce the possibility of an erroneous determination indicating that the inspection result is OK when similar drugs are prepared by mistake. In addition, since a similar range is set as an inspection target, it is possible to shorten the time required for image checking, compared with a case where image checking of all drugs registered in the drug database is performed. That is, it is possible to realize efficient inspection while suppressing erroneous determination.

BRIEF DESCRIPTION OF THE DRAWINGS

FIG. 2 is a diagram showing an example of information stored in a drug database.

FIG. 3 is a diagram showing the relationship between prescribed drugs and a drug image acquired by comparison target selection section.

FIG. 9 is a flowchart showing the operation procedure in the drug inspection system of the third embodiment.

DESCRIPTION OF THE PREFERRED EMBODIMENTS

Prior to the description of embodiments of the present invention, a schematic flow from the time of prescription of drugs by a doctor until the prepared drugs are handed to a patient will be described. After a prescription is written by a doctor, a pharmacist dispenses drugs specified in the prescription from packaging materials, such as a PTP (press through package), to a tray or the like one bag at a time. Alternatively, prescription information may be input into an automatic drug dispenser, and the automatic drug dispenser may dispense the drugs. A packaging device packages dispensed drugs, for example, for each specified dosage time according to prescription information. The packaged drugs are passed to the patient after final checking or the like by the pharmacist. The drug inspection apparatus of the present invention supports pharmacist inspection regarding whether or not the drugs passed to a patient are as prescribed.

Figure 1:
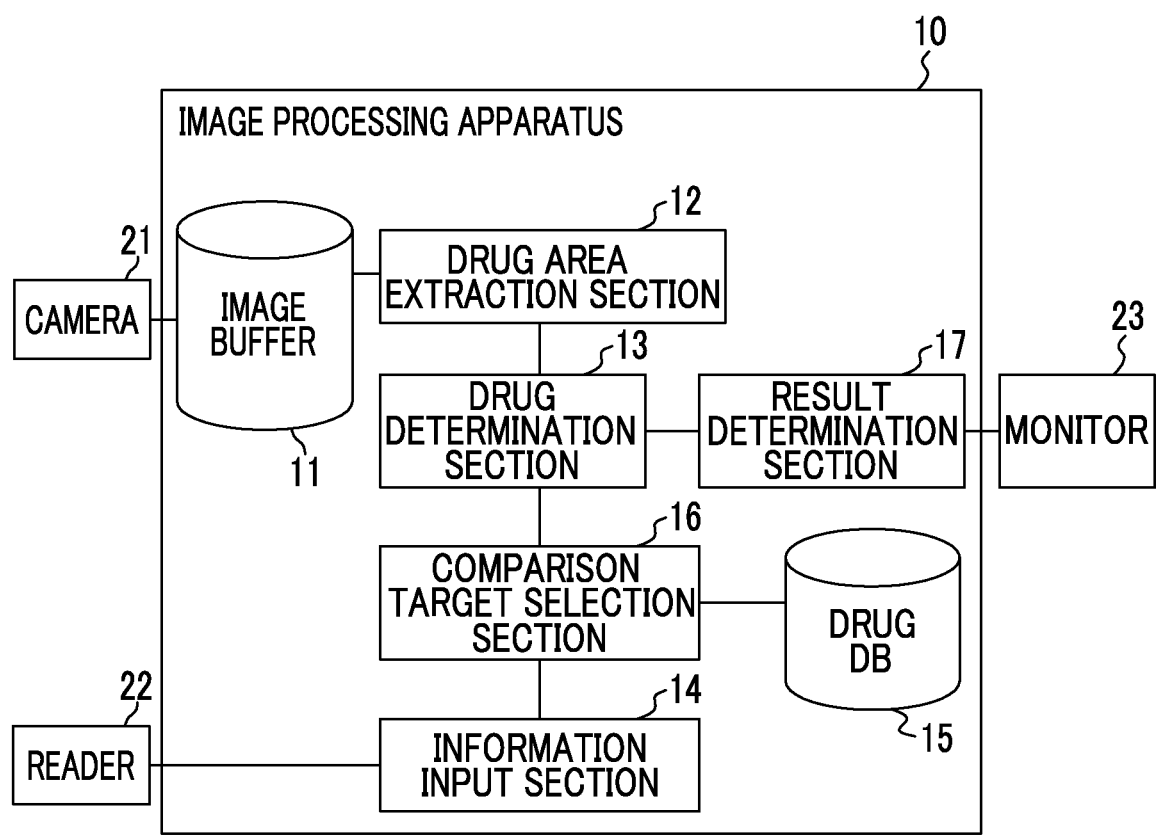
FIG. 1 is a block diagram showing the configuration of a drug inspection system including a drug inspection apparatus (image processing apparatus) of an embodiment of the present invention.

Hereinafter, embodiments of the present invention will be described in detail with reference to the diagrams. FIG. 1 shows the configuration of a drug inspection system including a drug inspection apparatus (image processing apparatus) of an embodiment of the present invention. The drug inspection system includes a drug inspection apparatus 10, an imaging apparatus (camera) 21, a reader 22, and a monitor 23. The drug inspection apparatus 10 includes an image buffer 11, a drug area extraction section 12, a drug determination section (first drug determination section) 13, an information input section 14, a drug database 15, a comparison target selection section 16, and an inspection result determination section 17.

In addition, the drug inspection apparatus 10 is a computer including a central processing unit (CPU), a main memory, and a nonvolatile storage device, for example. For example, when a program stored in the storage device is loaded to the main memory and the CPU executes the loaded program, each functional block of the drug area extraction section 12, the drug determination section (first drug determination section) 13, the information input section 14, the comparison target selection section 16, and the inspection result determination section 17 functions.

The camera 21 captures an image of packaged (prepared) drugs. For example, the camera 21 captures a prescription bag in which prepared drugs are packaged. Alternatively, drugs placed on a tray before being packaged may be captured. During the capturing the image, it is preferable to eliminate any overlapping between drugs by applying vibration, for example. The image buffer 11 stores a captured image that has been captured by the camera 21. The drug area extraction section 12 reads the captured image of drugs from the image buffer 11, and extracts a drug area portion from the captured image. For example, when a plurality of drugs are packaged in one prescription bag, the drug area extraction section 12 extracts the drugs so as to be separated from each other.

The reader 22 reads prescription information. For example, the reader 22 reads information, such as the prescribed drugs, the number of drugs, and the specified dosage time, from the prescription written on the paper by optical character recognition (OCR). When a bar code indicating the information regarding the prescribed drugs is present in the prescription, it is possible to read the bar code to read the information, such as prescribed drugs, the number of drugs, and specified dosage time. The information input section 14 receives the prescription information read by the reader 22. Alternatively, the information input section 14 may communicate with a computer, which is used by a doctor who has written the prescription, by cable or wirelessly, to receive the prescription information from the computer of the doctor. In addition, an operator may read a prescription and input the prescription information using a keyboard or the like.

In the drug database 15, various kinds of information regarding drugs that can be prepared are stored. Image information (drug images) of drugs is included in the information stored in the drug database 15. The comparison target selection section 16 acquires drug images of drugs, which should be prepared according to the prescription, and drugs similar thereto from the drug database 15. More specifically, the comparison target selection section 16 acquires drug images of drugs included in prescription information and drugs similar thereto from the drug database 15 based on the prescription information input from the information input section 14.

As drug images of drugs similar to prescribed drugs, the comparison target selection section 16 acquires drug images of drugs located at a distance within a predetermined threshold value from a position in the feature space of the prescribed drugs, for example. As features of drugs, a pattern feature indicating the brightness distribution on the drug surface including characters, an outer shape feature indicating a contour shape, a size feature indicating the area or the lengths of the long and short axes, a color feature, and the like can be considered. As another example, a list of drugs similar to each drug may be set in the drug database 15, and drug images of similar drugs may be acquired with reference to the list.

The drug determination section 13 that also serves as image checking means compares the captured image of the drug from the camera 21 with the drug image acquired from the drug database 15 by the comparison target selection section 16, and determines drugs present in the captured image and the number thereof. For example, the drug determination section 13 determines to which drug each drug area corresponds by extracting a feature amount from the image of each drug area extracted by the drug area extraction section 12 and comparing the feature amount with the feature amount extracted from the drug image acquired from the drug database 15. The drug determination section 13 determines that the drug with the closest feature amount is the drug of each drug image (captured image), for example.

Based on the prescription information, the inspection result determination section 17 determines whether or not the prepared drugs and the number thereof match the prescription information. For example, the inspection result determination section 17 determines whether or not the types of drugs and the number thereof are correct for each packaging. When it is determined that the prepared drugs and the number thereof match the prescription information, the inspection result determination section 17 displays an inspection result of OK on the monitor 23. Alternatively, using a printer (not shown), a display showing an inspection result of OK may be printed on the prescription bag or the like.

Here, a case can be considered in which, if a certain drug and another drug are too similar, both drugs cannot be clearly distinguished by image determination. Upon inspection of the drugs, a situation where the result of the inspection is OK is obtained even though the wrong drugs are packaged in fact should be avoided. Therefore, when the features are too similar and drugs that cannot be determined by image analysis are simultaneously prescribed, the inspection result determination section 17 may output "indistinguishable" as a determination result without performing image analysis.

For example, a list of drugs that cannot be determined by image analysis due to high similarity (simultaneously indistinguishable drug list) is stored in the drug database 15. The inspection result determination section 17 acquires the simultaneously indistinguishable drug list relevant to each prescribed drug from the drug database 15 with reference to the prescription information. When drugs included in the simultaneously indistinguishable drug list are prescribed at the same time, "indistinguishable" may be output without checking being performed by the drug determination section 13.

FIG. 2 shows an example of information stored in the drug database 15. The drug database 15 stores, for example, a drug ID, a drug name, a drug image, a similar drug list, and a simultaneously indistinguishable drug list for each drug. The drug ID is an identifier for uniquely identifying a drug, and the drug name is the name of a drug. In the similar drug list, IDs of one or more drugs similar to a drug identified by the drug ID are stored. In the example shown in FIG. 2, "drug A" is similar to "drug X" and "drug Y". In this case, when "drug A" is included in the prescription information, the comparison target selection section 16 acquires images of "drug X" and "drug Y" in addition to the image of "drug A".

In the simultaneously indistinguishable drug list, IDs of drugs that are difficult to be distinguished from a drug identified by the drug ID by image checking are stored. In the example shown in FIG. 2, "drug A" is too similar to names "drug D" and "drug E". Accordingly, "drug A" and the drug names "drug D" and "drug E" cannot be clearly determined by image checking with the drug determination section 13. When these drugs are prescribed at the same time, that is, when "drug A" and "drug D" or "drug E" are included in the prescription information, the inspection result determination section 17 may output the fact that determination is not possible.

FIG. 3 shows the relationship between prescribed drugs and drug images acquired by the comparison target selection section 16. For example, it is assumed that three drugs of drug A, drug B, and drug C have been prescribed in a prescription. When the information shown in FIG. 2 is stored in the drug database 15, the comparison target selection section 16 acquires drug images of the drug A, the drug B, and the drug C and drug images of drug X, drug Y, and drug Z similar thereto from the drug database 15. The drug determination section 13 compares the image of each drug area extracted by the drug area extraction section 12 with the drug image acquired by the comparison target selection section 16, and determines to which of the drugs A, B, C, X, Y, and Z, which are targets to be checked, the image of each drug area extracted by the drug area extraction section 12 corresponds based on the feature amount difference.

Figure 4:
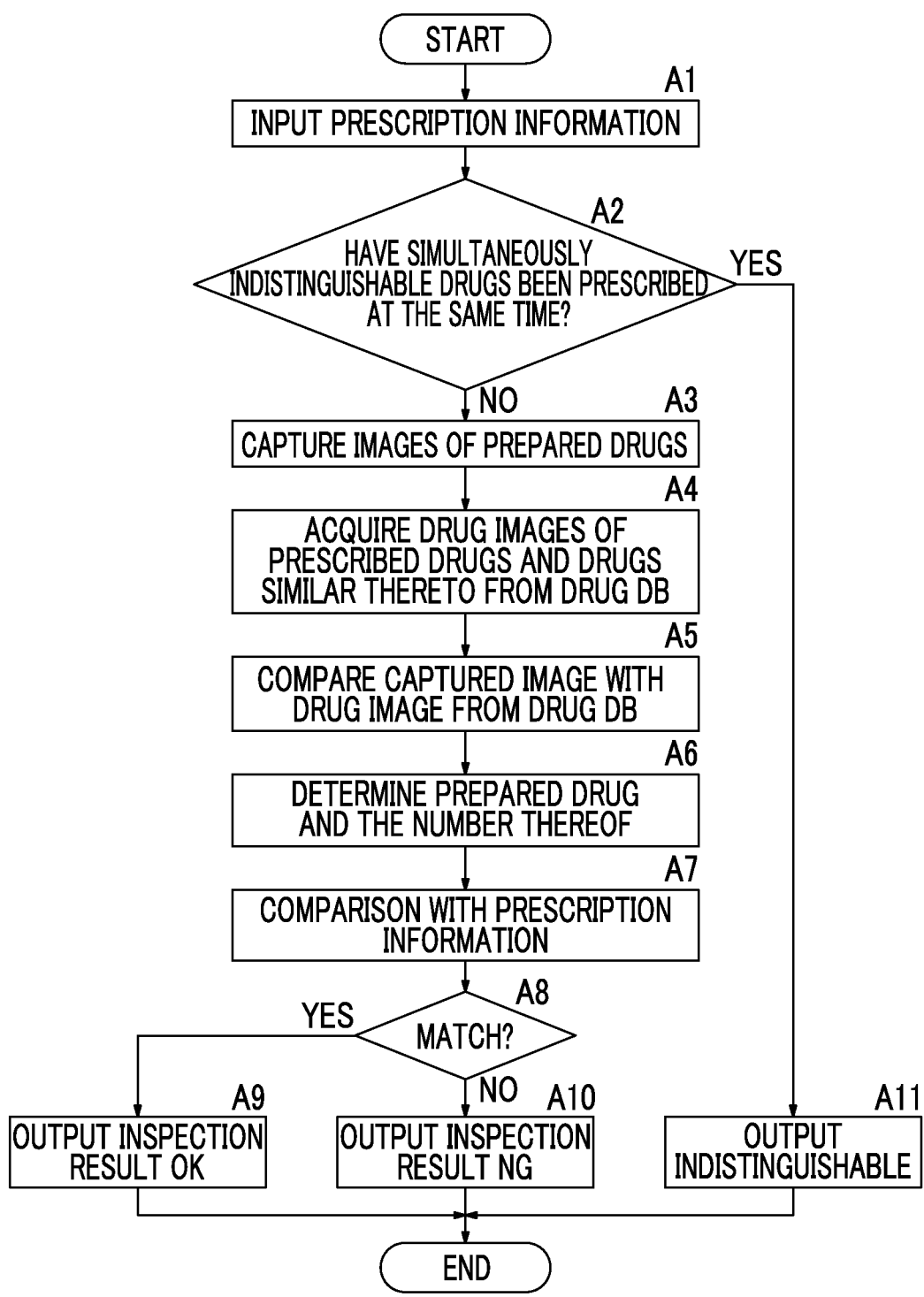
FIG. 4 is a flowchart showing the operation procedure of the drug inspection system of the first embodiment.

FIG. 4 shows the operation procedure of the drug inspection system of the first embodiment. The information input section 14 receives prescription information from the reader 22 (step A1). The inspection result determination section 17 checks whether or not simultaneously indistinguishable drugs have been prescribed at the same time with reference to the drug database 15 (step A2). For example, the inspection result determination section 17 checks whether or not other drugs included in the prescription information are included in the simultaneously indistinguishable drug list with reference to the simultaneously indistinguishable drug list (FIG. 2) corresponding to the drug included in the prescription information. When simultaneously indistinguishable drugs have been prescribed at the same time, the inspection result determination section 17 displays on the monitor 23 that determination is not possible (step A11). In addition, step A2 may be omitted.

The camera 21 captures drugs packaged by a packaging device or the like or drugs in a state where drugs to be packaged are placed on a tray corresponding to each prescription bag or the like (step A3). The captured image is stored in the image buffer 11. The comparison target selection section 16 acquires drug images (masters) of prescribed drugs and drugs similar thereto based on the prescription information input in step A1 (step A4). The checking range is expanded by acquiring not only the images of prescribed drugs but also the images of drugs similar thereto.

The drug area extraction section 12 extracts drug areas from the captured image that has been captured by the camera 21. The drug determination section 13 compares each of the extracted drug areas with each of the drug images acquired by the comparison target selection section 16 (step A5). The drug determination section 13 determines packaged drugs and the number thereof by comparing the feature amount extracted from the drug area with the feature amount extracted from the drug image acquired by the comparison target selection section 16 (step A6). For example, for each specified dosage time, the drug determination section 13 determines to which drug the drug packaged in a prescription bag corresponding to each specified dosage time corresponds and how many packs of the drug are present.

In addition, when a plurality of drug images having a feature amount close to the feature amount extracted from the drug area image are present as a result of comparison between the feature amount extracted from the drug area image and the feature amount extracted from the drug image (master) acquired by the comparison target selection section 16, the drug determination section 13 may determine that it is not possible to determine to which drug the target drug corresponds. For example, the drug determination section 13 calculates a feature amount difference between each drug image acquired by the comparison target selection section 16 and the drug area image, and specifies a drug image having the smallest feature amount difference (drug image most similar to the drug area image) and a drug image having the second smallest feature amount (drug image second similar to the drug area image). The feature amount difference between the drug image most similar to the drug area image and the drug area image may be compared with the feature amount difference between the drug image second most similar to the drug area image and the drug area image, and it may be determined that it is not possible to determine to which drug the drug of the drug area corresponds if both the differences are appropriately the same (for example, if the ratio of the feature amount differences is within a predetermined range or if the difference between the feature amount differences is within a predetermined range).

The inspection result determination section 17 compares the drugs and the number thereof determined in step A6 with the prescription information (step A7), and determines whether or not the drugs and the number thereof determined in step A6 match the prescription information (step A8). The inspection result determination section 17 determines whether or not the packaged drugs match the prescription information, for example, for each prescription bag. When the packaged drugs match the prescription information, the inspection result determination section 17 outputs an inspection result of OK to the monitor 23 (step A9). When the packaged drugs do not match the prescription information, the inspection result determination section 17 outputs an inspection result of NG to the monitor 23 (step A10). When displaying the inspection result, an image captured by the camera 21 may be displayed on the monitor 23. In step A6, when it is determined that the drugs cannot be determined as a result of the image checking done by the drug determination section 13, the inspection result determination section 17 may determine "indistinguishable" and display the result on the monitor 23.

When the inspection result determination section 17 determines that packaged drugs and the number thereof match the prescription information, printing for indicating that the inspection result is OK may be performed on a prescription bag corresponding to the drugs determined to match the prescription information. For example, after inspection with the drug inspection apparatus 10, information indicating the specified dosage time, such as morning, daytime, evening, or bedtime, or the names of drugs contained in a prescription bag and the number thereof may be printed on a prescription bag determined to have an inspection result of OK. Printing is preferably performed on a seal portion of the prescription bag, for example. A prescription bag determined to have an inspection result of NG is preferably cut from the line of prescription bags that are continuously located so that the inspection result OK and the inspection result NG are separated from each other.

When the drug inspection apparatus 10 determines the inspection result NG or indistinguishable, a printing apparatus may perform printing for indicating the inspection result NG or indistinguishable using ink invisible to the human eye, such as UV ink, for example. The pharmacist can see which prescription bag has an inspection result NG or is indistinguishable by using UV light or the like. The inspection result determination section 17 may prompt the pharmacist to check an image, which is obtained by capturing a prescription bag determined to have an inspection result of NG or to be indistinguishable, by displaying the image on the monitor 23 in an enlarged manner. The pharmacist re-inspects visually the prescription bag determined to have an inspection result of NG or to be indistinguishable, and inputs an inspection result of OK if it is confirmed that there is no error. In this case, a printing apparatus prints information indicating the specified dosage time, such as morning, daytime, evening, or bedtime, or the names of drugs contained in a prescription bag and the number thereof. Since the characters printed with UV ink are not visible to patients, it is not necessary to eliminate the print indicating that the inspection result is NG or indistinguishable even if the inspection result OK is obtained by re-inspection.

In the present embodiment, the comparison target selection section 16 acquires drug images of prescribed drugs and drug images of drugs similar to the prescribed drugs, as images to be compared, from the drug database 15. The drug determination section 13 compares the captured image of drugs, which has been captured by the camera 21, with the drug image acquired from the drug database 15 with the comparison target selection section 16, and determines the drugs and the number thereof. By expanding the image checking target to the range including not only drugs to be prepared according to the prescription but also drugs similar thereto, it is possible to reduce the possibility of erroneous determination indicating that the inspection result is OK even when similar drugs are prepared by mistake. In addition, since a similar range is set as an inspection target, it is possible to shorten the time required for image checking, compared with a case where image checking of all drugs registered in the drug database 15 is performed. Therefore, it is possible to increase the processing speed.

In addition, the drug inspection apparatus 10 may be configured so that, when a drug that is not registered in the drug database 15 is prescribed, the drug area image of the drug can be registered in the drug database 15. In addition, the drug database 15 does not necessarily need to be provided in the drug inspection apparatus 10, and a drug database provided remotely may be used instead of the drug database 15 provided in the drug inspection apparatus 10 or in addition to the drug database 15 provided in the drug inspection apparatus 10.

Figure 5:
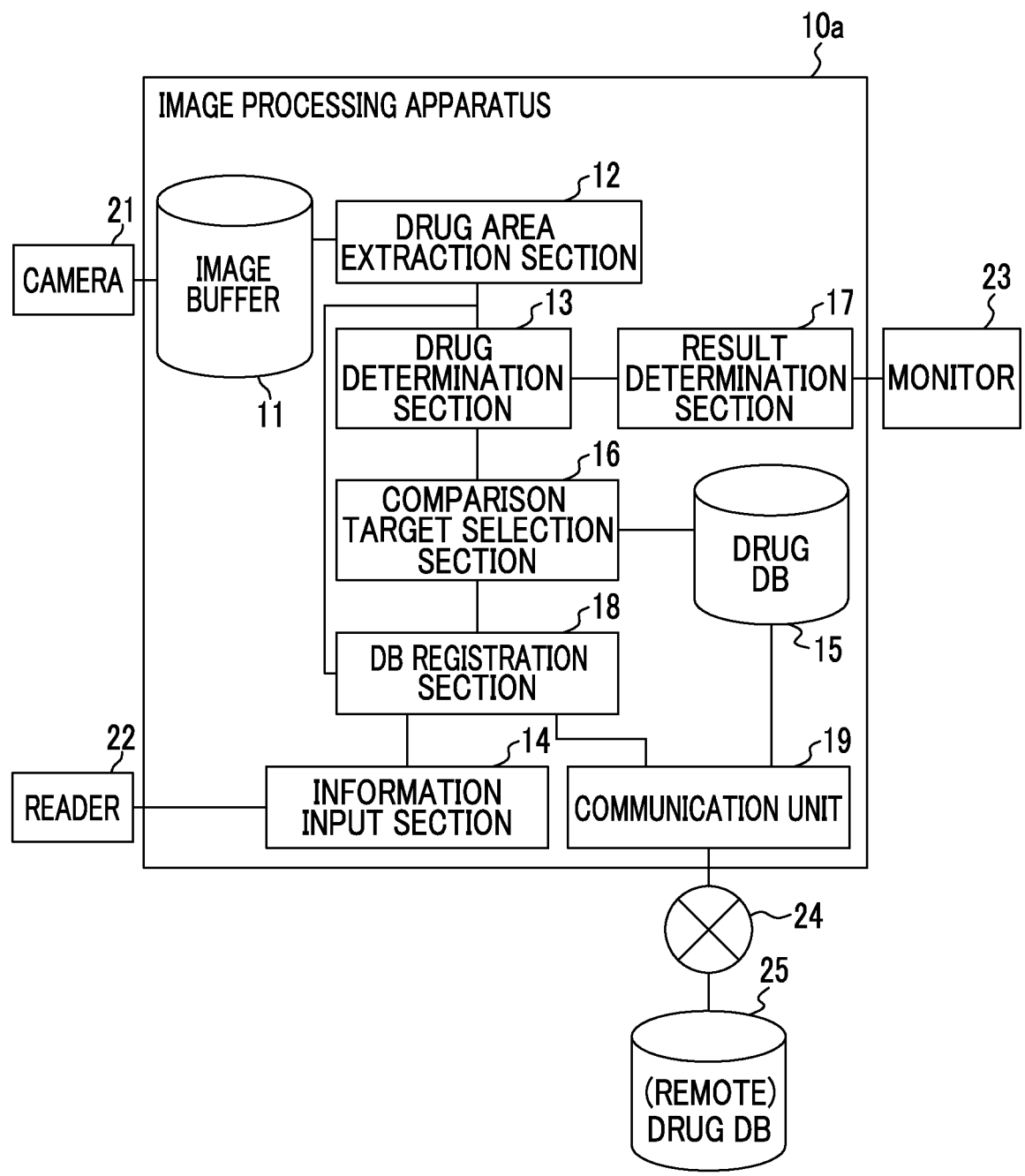
FIG. 5 is a block diagram showing a drug inspection apparatus of a modification example.

FIG. 5 shows a drug inspection apparatus of a modification example. A drug inspection apparatus 10a further includes a database registration section 18 and a communication unit 19. The database registration section 18 prompts a user to designate a partial image (drug area image) of a drug unregistered in the database, which is included in a captured image, when there is no information (drug images) of prescribed drugs in the drug database 15. The user selects and designates a drug unregistered in the database from each drug area image displayed on the monitor 23, for example. The database registration section 18 additionally registers the designated drug area image in the drug database 15, as a drug image of the drug, together with various kinds of information.

The communication unit 19 communicates with a remote drug database 25 through a network 24. The same information as in the (local) drug database 15 provided in the drug inspection apparatus 10 is registered in the drug database 25. For example, information on new drugs or information on drugs with a low frequency of use may not be present in the drug database 15 in the drug inspection apparatus 10, and may be present only in the remote drug database 25. When information regarding the prescribed drugs is not present in the local drug database 15, the comparison target selection section 16 accesses the remote drug database 15 through the communication unit 19 to acquire the drug image from the remote drug database 15. The drug image acquired at this time may be registered in the local drug database 15 by the database registration section 18.

Figure 6:
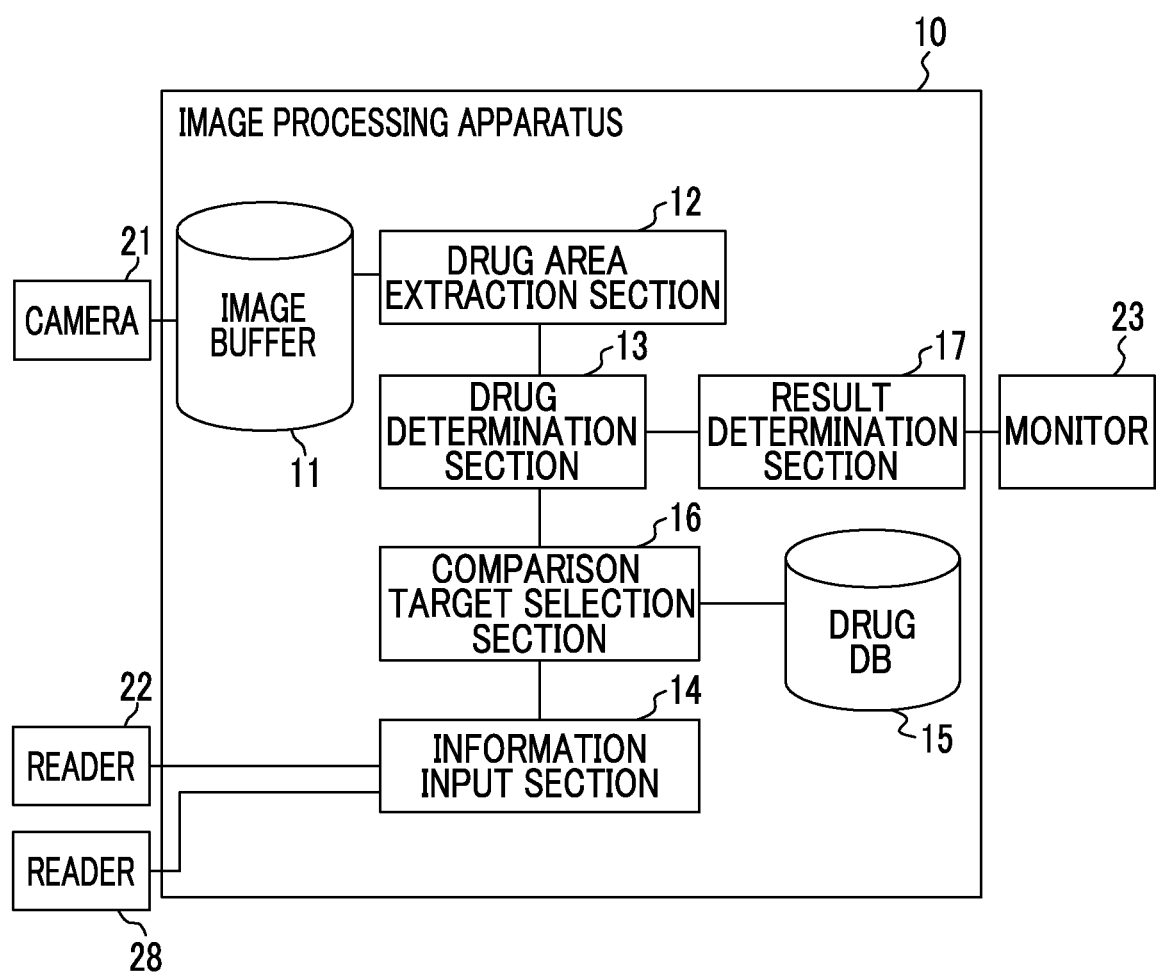
FIG. 6 is a block diagram showing a drug inspection system including a drug inspection apparatus of a second embodiment of the present invention.

Next, a second embodiment of the present invention will be described. FIG. 6 shows a drug inspection system including a drug inspection apparatus of the second embodiment of the present invention. The drug inspection system in the present embodiment includes a reader 28 that reads dispensing information for specifying drugs used at the time of at the time of packaging (preparation) in addition to the configuration of the drug inspection system of the first embodiment shown in FIG. 1. In the present embodiment, when acquiring the drug images of drugs to be packaged and drugs similar thereto, the dispensing information input from the reader 28 is used. The other points may be the same as those in the first embodiment.

The reader 28 acquires information for identifying the drugs dispensed according to prescription information, for example, from an automatic drug dispenser. Alternatively, it is possible to provide an RFID tag in a tray to dispense drugs, store information for identifying the dispensed drugs in the RFID tag when dispensing drugs, and read the dispensing information from the RFID tag. The information input section 14 receives the dispensing information read by the reader 28. Alternatively, the dispensing information may be directly received from the automatic drug dispenser by cable or wireless communication with the automatic drug dispenser. The comparison target selection section 16 acquires the drug images of drugs included in the prescription information and drugs similar thereto from the drug database 15.

In the packaging of drugs, dispensed drugs are packaged in a prescription bag. Accordingly, if there is no mistake in dispensing, dispensed drugs should be able to be correctly packaged basically as prescribed. However, it cannot be said that there is no probability of a mistake. In the present embodiment, by performing inspection in a checking range that is expanded to include drugs similar to dispensed drugs, it is possible to correctly check whether or not drugs are packaged as prescribed. Therefore, it is possible to prevent mistakes that may occur during the period from dispensing to packaging. The other effects are the same as in the first embodiment.

Figure 7:
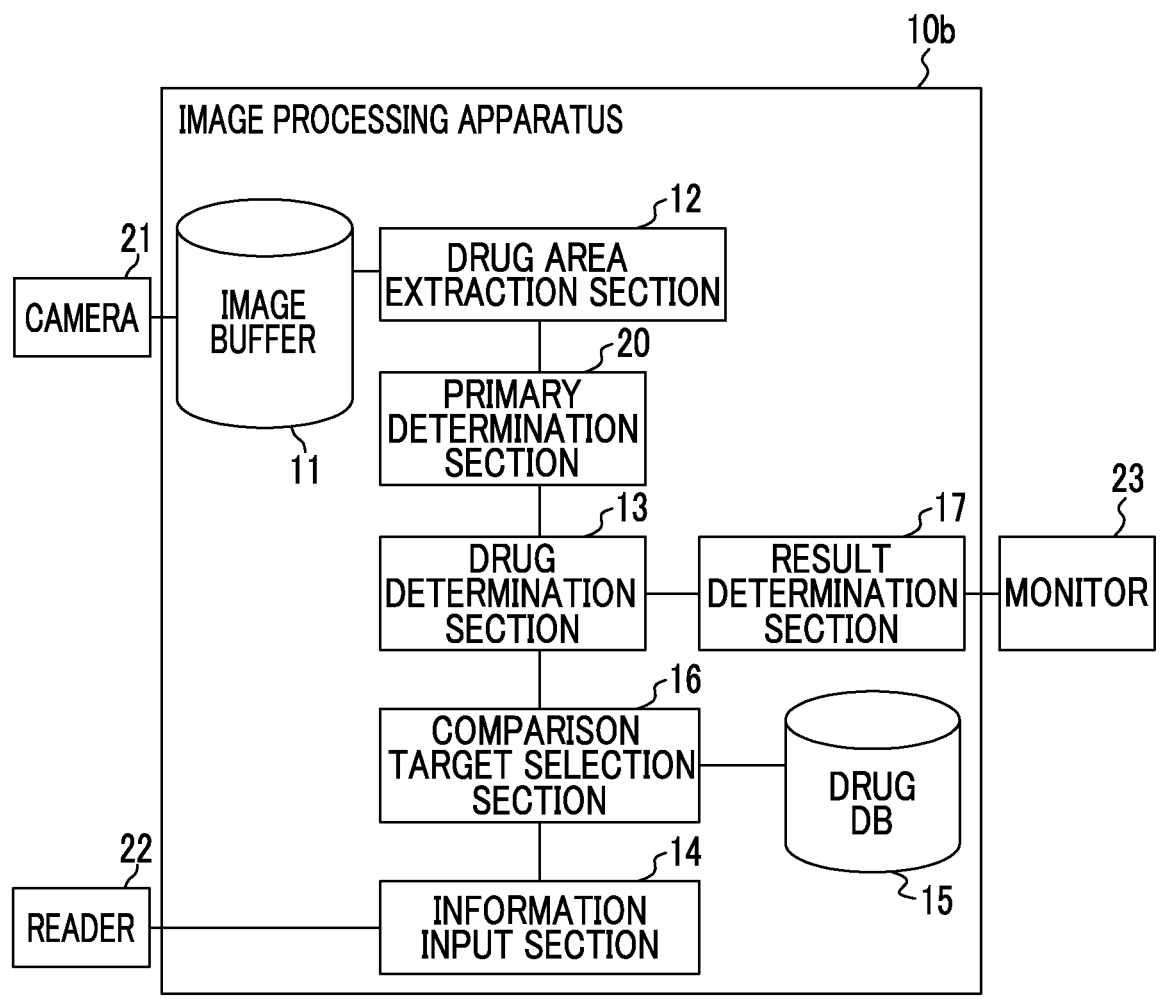
FIG. 7 is a block diagram showing a drug inspection system including a drug inspection apparatus of a third embodiment of the present invention.

Next, a third embodiment of the present invention will be described. FIG. 7 shows a drug inspection system including a drug inspection apparatus of the third embodiment of the present invention. A drug inspection apparatus 10b of the present embodiment includes a primary determination section (second drug determination section) 20 in addition to the configuration of the drug inspection apparatus 10 of the first embodiment shown in FIG. 1.

Figure 8:
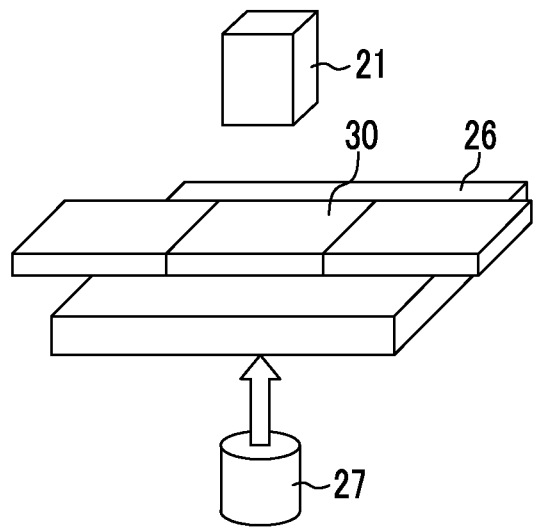
FIG. 8 is a diagram showing the capturing of a prescription bag by a camera.

The primary determination section 20 performs the primary determination of drugs by extracting the outer shape feature and the size feature of each drug from the captured image of prepared drugs and comparing the extracted outer shape feature and size feature with the outer shape feature and the size feature of each drug to be prepared. For example, the primary determination is performed for drugs that can be determined based on the outer shape feature and the size feature. For example, the primary determination section 20 checks whether or not two or more drugs having similar outer shape features and size features are included in the prescription information. When drugs having similar outer shape features and size features are included, the primary determination section 20 determines that the two or more similar drugs cannot be determined by the primary determination, and excludes the drugs from the primary determination targets. It is also possible to perform primary determination using a color feature in addition to the outer shape feature and the size feature. The drug determination section 13 compares captured images with drug images (masters) acquired from the drug database 15 in detail for the drugs that cannot be determined by the primary determination section 20.

captured images used in the drug determination section 13 and the primary determination section 20 may be different. FIG. 8 shows the capturing of a prescription bag by the camera 21. For example, a prescription bag 30 is transported onto an inspection table 26, and drugs contained in the prescription bag 30 are captured by the camera 21. In FIG. 8, a light 27 is provided at a position facing the camera 21 with the inspection table 26 having optical transparency interposed therebetween. The camera 21 performs the image capturing in two states of a state where the light 27 is turned on and a state where the light is turned off (state where light from the camera 21 side is emitted to the prescription bag 30). By turning on the light 27 to perform an image capturing, the silhouette of drugs appears in the captured image. Accordingly, the outer shape and size of drugs become clearer.

The drug area extraction section 12 extracts a drug area from the captured image (transmitted illumination captured image) captured where the light 27 is turned on, and transmits the extracted drug area to the primary determination section 20. In addition to drug images, the outer shape feature and the size feature of each drug are stored in the drug database 15. Accordingly, the primary determination section 20 acquires the outer shape features and the size features of drugs included in the prescription information from the drug database 15. The primary determination section 20 performs the primary determination of drugs and the number thereof by extracting the outer shape feature and the size feature of each drug from the transmitted illumination captured image and comparing these features with the outer shape feature and the size feature acquired from the drug database 15.

In addition, the drug area extraction section 12 extracts a drug area from a normal captured image captured where the light 27 is turned off and transmits the extracted drug area to the drug determination section 13. The comparison target selection section 16 acquires drug images of drugs that have not been determined by the primary determination section 20, among the drugs included in the prescription information, and drug images of drugs similar thereto. The drug determination section 13 determines which drugs have not been determined in the primary determination and the number thereof by comparing the image of each drug area with the drug image acquired by the comparison target selection section 16. In addition, as in the second embodiment, the comparison target selection section 16 may use dispensing information instead of prescription information.

FIG. 9 shows the operation procedure in the drug inspection system of the third embodiment. The information input section 14 receives prescription information from the reader 22 (step B1). The inspection result determination section 17 checks whether or not simultaneously indistinguishable drugs have been prescribed at the same time with reference to the drug database 15 (step B2). For example, the inspection result determination section 17 checks whether or not other drugs included in the prescription information are included in the simultaneously indistinguishable drug list with reference to the simultaneously indistinguishable drug list (FIG. 2) corresponding to the drug included in the prescription information. When simultaneously indistinguishable drugs have been prescribed at the same time, the inspection result determination section 17 displays on the monitor 23 that determination is not possible (step B14). In addition, step B2 may be omitted.

The camera 21 captures drugs packaged by a packaging device or the like or drugs in a state where drugs to be packaged are placed on a tray corresponding to each prescription bag or the like (step B3). In step B3, the camera 21 may capture the silhouette of drugs by emitting light to the drugs from the opposite side. The drug area extraction section 12 extracts a drug area from the captured image (transmitted illumination captured image) captured in step B3.

The primary determination section 20 specifies drugs that can be determined from the outer shape features and the size features with reference to the prescription information. For example, when only one drug of a plurality of packaged drugs has a long outer shape in one direction, such as a capsule, it is easy to determine a capsule-shaped drug among the plurality of packaged drugs. On the other hand, when a plurality of drugs that have shapes, such as flat round tablets, and have similar sizes are included in the plurality of packaged drugs, it is difficult to correctly determine these drugs from the outer shape features and the size features. The primary determination section 20 sets drugs for which drugs having similar outer shape features and size features are not present, among the drugs included in the prescription information, as primary determination targets, and determines the other drugs as drugs that cannot be determined in the primary determination (that are excluded from the determination range).

The primary determination section 20 acquires the outer shape features and the size features of drugs, which are primary determination targets, from the drug database 15. The primary determination section 20 extracts the outer shape feature and the size feature from each drug area extracted from the drug area extraction section 12, and compares these features with the outer shape feature and the size feature acquired from the drug database 15. The primary determination section 20 determines that the drug having the smallest feature amount difference is a drug of each drug area (step B4). In this case, when a plurality of drugs having approximately the same feature amount differences are present, "indistinguishable" may be determined. For specific drugs set as the primary determination targets, the primary determination section 20 determines how many specific drugs have been packaged.

After the primary determination, detailed second determination based on image checking is performed for the drugs that could not be determined in the primary determination. The camera 21 captures drugs packaged by a packaging device or the like or drugs in a state where drugs to be packaged are placed on a tray corresponding to each prescription bag or the like (step B5). In this case, no light is emitted from the opposite side to the camera 21, and the color of a drug or the character, pattern, or the like attached to the drug can be visually recognized in the captured image. In addition, when the transmitted illumination captured image is not used in the primary determination, step B5 may be omitted, and the primary determination and the second determination may be performed using the same captured image. The comparison target selection section 16 acquires drug images (masters) of drugs that have not been determined in the primary determination, among the prescribed drugs, and drug images (masters) of drugs similar thereto (step B6). Since some drugs are determined in the primary determination, it is possible to reduce the number of drugs for which detailed image checking is performed.

The drug area extraction section 12 extracts a drug area from the captured image captured in step B5. The drug determination section 13 compares each of the extracted drug areas excluding the drug areas determined in the primary determination with each of the drug images acquired by the comparison target selection section 16 (step B7). The drug determination section 13 determines drugs, which have not been determined in the primary determination, and the number thereof by comparing the feature amount extracted from the drug area with the feature amount extracted from the drug image acquired by the comparison target selection section 16 (step B8). In addition, when all drugs can be determined in the primary determination, steps B5 to B8 can be omitted.

The inspection result determination section 17 compares the drugs and the number thereof determined in steps B4 and B8 with the prescription information (step B9), and determines whether or not the drugs and the number thereof determined in steps B4 and B8 match the prescription information (step B10). The inspection result determination section 17 determines whether or not packaged drugs match the prescription information, for example, for each prescription bag. When the packaged drugs match the prescription information, the inspection result determination section 17 outputs an inspection result of OK to the monitor 23 (step B11). When the packaged drugs do not match the prescription information, the inspection result determination section 17 outputs an inspection result of NG to the monitor 23 (step B12). When displaying the inspection result, at least one of the images captured in steps B3 and B5 may be displayed on the monitor 23.

In the present embodiment, drugs that can be determined from the outer shape features and the size features are determined by the primary determination section 20, and image checking for drugs that cannot be determined by the primary determination section 20 (drugs that are not determination targets) is performed by the drug determination section 13. Determination of drugs based on the outer shape features and the size features can be performed more easily than determination based on image checking. In the present embodiment, since the number of drugs that are image checking targets can be reduced using the primary determination section 20, it is possible to perform drug determination more efficiently by reducing the number of image checking targets. The other effects are the same as those of the first and second embodiments.

In addition, the drug determination section 13 may include character recognition means for extracting characters from an image and recognizing the characters. For example, it is also possible to extract a drug name or a character string unique to a drug from a captured image, recognize the drug name or the character string, and determine drugs present in the captured image based on the recognized character. In addition, although one camera is shown in FIG. 8, two cameras may be provided in the third embodiment so that a captured image in a state where the light 27 is turned on and a captured image in a state where the light 27 is turned off are captured by separate cameras.

While the present invention has been described based on the preferred embodiments, the drug inspection apparatus and method of the present invention is not limited only to the embodiments described above, and various modifications and changes to the configuration of the embodiments described above are also included in the range of the present invention.

What is claimed is:

1. A drug inspection apparatus for inspecting drugs that are prepared based on prescription information and are packaged in a prescription bag, comprising:
    a processor configured to
        acquire drug images of only drugs that should be prepared according to a prescription from a drug database that stores drug images of drugs that can be prepared and only drugs similar to the drugs that should be prepared according to the prescription from the drug database;
        determine not to perform an image comparison based on a determination that the prepared drugs and the number of the prepared drugs are determined to be simultaneously indistinguishable from different drugs in the drug database;

perform a comparison of a captured image obtained by capturing an image of the prepared drugs with the drug images acquired from the drug database and determining to which drug each drug present in the captured image corresponds and a number of drugs, in a case in which the plurality of drugs are prescribed at the same time in the prescription; and determine whether or not the prepared drugs and a number of the prepared drugs match the prescription information based on the prescription information and output a result of the determination whether or not the prepared drugs and the number thereof match the prescription information, wherein the processor acquires drug images of drugs, which are located at a distance within a predetermined threshold value from a position in a feature space of physical characteristics of prepared drugs, as the drug images of the drugs similar to the prepared drugs.

2. The drug inspection apparatus according to claim 1, wherein the captured image is an image obtained by capturing an image of the prescription bag in which the prepared drugs are packaged.

3. The drug inspection apparatus according to claim 1, wherein drugs to be taken at each specified dosage time are packaged in the prescription bag.

4. The drug inspection apparatus according to claim 3, wherein the processor determines whether or not the drugs packaged in the prescription bag and the number of drugs match the prescription information for each specified dosage time.

5. The drug inspection apparatus according to claim 1, wherein the processor extracts characters from the captured image, recognizes the characters, and determines drugs present in the captured image based on the recognized characters.

6. The drug inspection apparatus according to claim 1, wherein the processor compares a first feature amount difference between the captured image and a first drug image having a feature amount closest to a feature amount extracted from the captured image with a second feature amount difference between the captured image and a second drug image having a feature amount second closest to the feature amount extracted from the captured image and determines that drug determination is not possible when both the first and second feature amount differences are approximately the same, and the processor determines that determination regarding whether or not the prepared drugs and the number thereof match the prescription information is not possible.

7. The drug inspection apparatus according to claim 1, wherein, when the processor determines that the determination regarding whether or not the prepared drugs and the number thereof match the prescription information is not possible, an indication that the determination is not possible is printed on a prescription bag corresponding to a drug determined to be indistinguishable using ink that cannot be visually recognized under visible light.

8. The drug inspection apparatus according to claim 1, wherein, when the processor determines that the determination regarding whether or not the prepared drugs and the number thereof match the prescription information is not possible, the captured image and a drug image from the drug database are displayed to prompt a user to input a checking result.

9. The drug inspection apparatus according to claim 1, wherein the processor acquires drug images of drugs included in the prescription information and drugs similar to the drugs included in the prescription information from the drug database based on the prescription information.

10. The drug inspection apparatus according to claim 1, wherein the comparison target selection section acquires, based on dispensing information for specifying drugs used at the time of preparation, drug images of drugs included in the dispensing information and drugs similar to the drugs included in the dispensing information from the drug database.

11. The drug inspection apparatus according to claim 1, wherein a list of drugs similar to each drug is stored in the drug database, and the processor acquires the drug images of the drugs similar to the prepared drugs with reference to the list of similar drugs.

12. The drug inspection apparatus according to claim 1, further comprising:

a second drug determination section configured to perform primary drug determination by extracting an outer shape feature and a size feature of each drug from the captured images of the prepared drugs and comparing the extracted outer shape feature and the extracted size feature with an outer shape feature and a size feature of each of the drugs to be prepared, wherein the first drug determination section compares the captured image with the drug image acquired from the drug database for each drug that cannot be determined by the second drug determination section.

13. The drug inspection apparatus according to claim 12, wherein the second drug determination section extracts an outer shape feature and a size feature from a captured image that is captured by emitting illumination light to the prepared drugs from an opposite side to imaging means.

14. The drug inspection apparatus according to claim 12, wherein, when two or more drugs having similar outer shape features and size features are included in the prescription information, the second drug determination section determines the two or more similar drugs to be indistinguishable drugs.

15. The drug inspection apparatus according to claim 1, wherein, when the processor determines that the prepared drugs and the number thereof match the prescription information, printing for indicating that an inspection result is OK is performed on a prescription bag corresponding to drugs determined to match the prescription information.

16. The drug inspection apparatus according to claim 1, wherein, when the processor determines that the prepared drugs and the number thereof do not match the prescription information, printing for indicating that an inspection result is NG is performed on a prescription bag corresponding to drugs determined not to match the prescription information using ink that cannot be visually recognized under visible light.

17. The drug inspection apparatus according to claim 1, wherein, when the processor determines that the prepared drugs and the number thereof do not match the prescription information, the captured image and a drug image from the drug database are displayed to prompt a user to input a checking result.

18. The drug inspection apparatus according to claim 1, further comprising:
a database registration section configured to prompt a user to designate a partial image of each prepared drug included in the captured image and additionally registering the designated partial image in the drug database when there is no drug image of the prepared drugs in the drug database.

19. The drug inspection apparatus according to claim 1, further comprising:
a database registration section configured to acquire drug images of the prepared drugs by accessing a remote master database when there is no drug image of the prepared drugs in the drug database.

20. A drug inspection method for inspecting drugs that are prepared based on prescription information and are packaged in a prescription bag using a drug inspection apparatus, the method comprising:
acquiring drug images of only drugs prepared according to a prescription from a drug database that stores drug images of drugs that can be prepared and only drugs similar to the drugs prepared according to the prescription from the drug database, by the drug inspection apparatus;
determining not to perform an image comparison based on a determination that the prepared drugs and the number of the prepared drugs are determined to be simultaneously indistinguishable from different drugs in the drug database and outputting a result of the determination not to perform the image comparison;
comparing a captured image obtained by capturing an image of the prepared drugs with the drug images acquired from the drug database and determining to which drug each drug present in the captured image corresponds and the number of drugs by the drug inspection apparatus, in a case in which the plurality of drugs are prescribed at the same time in the prescription; and
determining whether or not the prepared drugs and a number of the prepared drugs match the prescription information based on the prescription information by the drug inspection apparatus,
wherein drug images of drugs, which are located at a distance within a predetermined threshold value from a position in a feature space of physical characteristics of prepared drugs, are acquired as the drug images of the drugs similar to the prepared drugs.

* * * * *